(12) United States Patent
Stewart et al.

(10) Patent No.: US 12,042,211 B2
(45) Date of Patent: Jul. 23, 2024

(54) FLEXIBLE NECK FOR SURGICAL INSTRUMENTS

(71) Applicant: Cilag GmbH International, Zug (CH)

(72) Inventors: Randolph C. Stewart, Cincinnati, OH (US); Geoffrey S. Strobl, Williamsburg, OH (US); Barry Worrell, Dayton, OH (US)

(73) Assignee: Cilag GmbH International, Zug (CH)

( * ) Notice: Subject to any disclaimer, the term of this patent is extended or adjusted under 35 U.S.C. 154(b) by 302 days.

(21) Appl. No.: 17/394,805

(22) Filed: Aug. 5, 2021

(65) Prior Publication Data

US 2021/0361348 A1    Nov. 25, 2021

Related U.S. Application Data

(63) Continuation of application No. 16/227,085, filed on Dec. 20, 2018, now Pat. No. 11,096,739, which is a
(Continued)

(51) Int. Cl.
*B23P 15/00* (2006.01)
*A61B 17/29* (2006.01)
(Continued)

(52) U.S. Cl.
CPC .......... *A61B 18/1445* (2013.01); *A61B 17/29* (2013.01); *A61B 18/1482* (2013.01);
(Continued)

(58) Field of Classification Search
CPC ..................................................... B23P 15/00
See application file for complete search history.

(56) References Cited

U.S. PATENT DOCUMENTS

| 4,834,095 A | 5/1989 | Miller |
| 5,397,304 A | 3/1995 | Truckai |

(Continued)

FOREIGN PATENT DOCUMENTS

| CN | 1726874 A | 2/2006 |
| CN | 100579467 C | 1/2010 |

(Continued)

*Primary Examiner* — Sarang Afzali
(74) *Attorney, Agent, or Firm* — Mintz, Levin, Cohn, Ferris, Glovsky and Popeo, P.C.

(57) ABSTRACT

Methods of manufacturing a medical device are provided, which include injection molding a substantially cylindrical monolithic outer shell having an inner lumen and a plurality of ribs spaced longitudinally and extending partially circumferentially around the substantially cylindrical monolithic outer shell with elongate slots separating each rib. At least one flexible divider can be injection molded and advanced into the inner lumen to separate the inner lumen into first and second elongate channels and can be freely slidable relative to the substantially cylindrical monolithic outer shell. Proximal and distal ends of the substantially cylindrical monolithic outer shell can be respectively mated to a distal end of the elongate shaft and a proximal end of an end effector. First and second articulation bands can be advanced through the elongate shaft and channels and mated to opposed sides of the end effector.

6 Claims, 11 Drawing Sheets

Related U.S. Application Data continuation of application No. 14/659,037, filed on Mar. 16, 2015, now Pat. No. 10,172,670.

(51) Int. Cl.
*A61B 18/14* (2006.01)
*A61B 17/00* (2006.01)

(52) U.S. Cl.
CPC ..... *B23P 15/00* (2013.01); *A61B 2017/00309* (2013.01); *A61B 2017/00526* (2013.01); *A61B 2017/00986* (2013.01); *A61B 2017/2927* (2013.01); *A61B 2018/1455* (2013.01)

(56) References Cited

U.S. PATENT DOCUMENTS

| | | | |
|---|---|---|---|
| 5,632,432 A | 5/1997 | Schulze et al. | |
| 5,704,534 A | 1/1998 | Huitema et al. | |
| 6,491,626 B1 | 12/2002 | Stone et al. | |
| 7,918,376 B1 | 4/2011 | Knodel et al. | |
| 8,096,457 B1 | 1/2012 | Manoux et al. | |
| 8,568,390 B2 * | 10/2013 | Mueller | A61B 18/1445 606/1 |
| 9,295,514 B2 * | 3/2016 | Shelton, IV | A61B 18/082 |
| 10,159,506 B2 | 12/2018 | Boudreaux et al. | |
| 10,172,670 B2 | 1/2019 | Stewart et al. | |
| 10,932,846 B2 * | 3/2021 | Otrembiak | A61B 18/1445 |
| 2006/0022015 A1 | 2/2006 | Shelton, IV et al. | |
| 2006/0025811 A1 | 2/2006 | Shelton, IV | |
| 2009/0202387 A1 | 8/2009 | Dlugos, Jr. et al. | |
| 2012/0074200 A1 | 3/2012 | Schmid et al. | |
| 2012/0078243 A1 | 3/2012 | Worrell et al. | |
| 2012/0078247 A1 | 3/2012 | Worrell et al. | |
| 2013/0023868 A1 | 1/2013 | Worrell et al. | |
| 2014/0038151 A1 | 2/2014 | Hart | |
| 2016/0270839 A1 | 9/2016 | Stewart et al. | |
| 2019/0125434 A1 | 5/2019 | Stewart et al. | |

FOREIGN PATENT DOCUMENTS

| | | |
|---|---|---|
| CN | 103118618 A | 5/2013 |
| CN | 104287787 A | 1/2015 |
| EP | 1621137 A2 | 2/2006 |

* cited by examiner

FLEXIBLE NECK FOR SURGICAL INSTRUMENTS

CROSS-REFERENCE TO RELATED APPLICATIONS

This application is a continuation of U.S. patent application Ser. No. 16/227,085 (now U.S. Pat. No. 11,096,739), entitled "Flexible Neck for Surgical Instruments," filed on Dec. 20, 2018, which is a continuation of U.S. patent application Ser. No. 14/659,037 (now U.S. Pat. No. 10,172,670), entitled "Flexible Neck for Surgical Instruments," filed on Mar. 16, 2015, which are hereby incorporated by reference herein in their entireties.

FIELD

Methods and devices are provided for allowing articulation of an end effector on a surgical instrument.

BACKGROUND

Minimally invasive surgical techniques such as endoscopies and laparoscopies are often preferred over traditional surgeries because the recovery time, pain, and surgery-related complications are typically less with minimally invasive surgical techniques. Rather than cut open large portions of the body in order to access inner cavities, surgeons either rely on natural orifices of the body or create one or more small orifices in which surgical instruments can be inserted to allow surgeons to visualize and operate at the surgical site.

Some minimally invasive procedures can require that a working end of a device, which is inserted into the body, be articulated to angularly reorient the working end relative to the tissue. During such a procedure, for example, it is often necessary to position the working end at an angle relative to a shaft of the device, while still allowing the working end to performing various functions. Thus, surgical devices can include a flexible portion of a shaft that allows the end effector coupled thereto to articulate. Manufacturing the flexible portion typically involves making separate parts that can require multiple steps to assemble. Also, the multiple parts need to be reliably held together, and additional labor and costs can be expended to achieve this. Furthermore, it may be challenging to design and manufacture a flexible portion that has sufficient flexibility while maintaining sufficient rigidity and allowing proper control over articulation of the end effector.

Accordingly, there remains a need for improved methods and devices for allowing articulation of an end effector on a surgical instrument.

SUMMARY

Various methods and devices are provided for allowing articulation of an end effector on a surgical instrument. In one embodiment, a surgical device is provided having an elongate shaft with a longitudinal axis and a flexible portion extending along a length thereof. The flexible portion includes a substantially cylindrical monolithic outer shell having an inner lumen extending therethrough and defining a longitudinal axis, and a flexible divider separate from the shell and disposed within and extending through the inner lumen of the shell such that the divider separates the inner lumen into at least first and second elongate channels. The divider can be freely longitudinally slidable relative to the outer shell while being constrained from moving away from the longitudinal axis. The flexible portion can also include a first articulation member extending through the first elongate channel in the inner lumen of the shell, a second articulation member extending through the second elongate channel in the inner lumen of the shell, and an end effector coupled to a distal end of the elongate shaft and coupled to the first and second articulation members such that axial translation of the articulation members within the first and second elongate channels is effective to cause the flexible neck to bend such that the end effector can be oriented to extend transverse to a longitudinal axis of the elongate shaft.

The outer shell can have a variety of configurations, and in one embodiment the outer shell has an upper spine and a lower spine, each extending along at least a portion of a length of the outer shell. The outer shell can further include a first plurality of spaced arcuate ribs extending between the upper and lower spines along a first side of the outer shell, and a second plurality of spaced arcuate ribs extending between the upper and lower spines along a second side of the outer shell. In one embodiment, the divider can extend between the upper and lower spines of the outer shell. The dimensions of the outer shell can also vary, and in one embodiment a diameter of the outer shell can decrease from a proximal end thereof to a distal end thereof.

The arcuate ribs can also have various configurations, and in one aspect each of the first plurality of spaced arcuate ribs includes a cut-out formed on an internal surface thereof that seats the first articulation member, and each of the second plurality of spaced arcuate ribs includes a cut-out formed on an internal surface thereof that seats the second articulation member. Each of the first and second plurality of spaced arcuate ribs can have a constant width along an entire length thereof. In other embodiments, each of the first and second plurality of spaced arcuate ribs has a mid-portion with a width that is greater than a width at an end portion adjacent to each of the upper and lower spines. The upper and lower spines can also have various shapes and sizes, and in one embodiment the spines can each have a width at a proximal end thereof that is greater than a width at a distal end thereof.

The divider can also have a variety of configurations, and in one embodiment the divider can comprise first and second elongate members defining first and second pathways therebetween. The first and second elongate members can be freely longitudinally slidable relative to one another. An inner surface of each of the upper and lower spines can include a mating feature formed therein and configured to non-fixedly retain the divider. In another embodiment, each divider can include a plurality of brackets formed on an external surface thereof and spaced from one another along a longitudinal length of the divider. The plurality of brackets can prevent movement of the first and second articulation members toward the longitudinal axis while allowing free longitudinal sliding movement of the first and second articulation members. At least one of the plurality of brackets can define a longitudinal pathway extending therethrough, and the device can further include an electrically conductive member extending through the elongate shaft and through the pathway formed by the plurality of brackets. In another embodiment, at least one of the first and second elongate members that form the divider can include at least one protrusion configured to maintain the first and second elongate members at a predetermined distance apart along a length thereof.

The device can also include various other components, such as a knife member extending through the first pathway and an actuation band extending through the second pathway. The device can also include a conductive member extending through the elongate shaft and the inner lumen of the outer shell. The end effector on the device can also vary, and in one embodiment the end effector can include first and second jaws that are movable relative to one another.

In another embodiment, a flexible neck assembly is provided for allowing articulation of an end effector coupled to an elongate shaft of a medical device. The flexible neck assembly can be formed from a substantially cylindrical monolithic outer shell defining an inner lumen extending longitudinally therethrough. The outer shell can have an upper spine and an opposed lower spine, each extending along at least a portion of a length of the shell. A first plurality of arcuate ribs can be spaced longitudinally along a first side of the shell and can extend between the upper and lower spines. A second plurality of arcuate ribs can be spaced longitudinally along a second side of the shell opposite to the first side of the shell. The second plurality of arcuate ribs can extend between the upper and lower spines. Each rib of the first and second plurality of ribs can extend at least partially around a circumference of the shell. A flexible divider member separate from the shell can be freely slidably disposed within and extending through the inner lumen of the shell such that the divider extends between the upper and lower spines of the shell and separates the inner lumen into first and second elongate channels.

In one aspect, the divider can be in the form of first and second elongate members defining first and second pathways therebetween. The first and second elongate members can have spacers formed thereon that maintain the first and second elongate members at a predetermined distance apart. The first and second elongate members can also include a plurality of brackets formed on an external surface thereof and spaced from one another along a longitudinal length thereof. Each of the first plurality of spaced arcuate ribs can include a cut-out formed on an internal surface thereof that is configured to seat a first articulation member, and each of the second plurality of spaced arcuate ribs can include a cut-out formed on an internal surface thereof that is configured to seat a second articulation member. While the configuration of each rib can vary, in one embodiment each of the first and second plurality of spaced arcuate ribs has a constant width along an entire length thereof. In another embodiment, each of the first and second plurality of spaced arcuate ribs has a mid-portion with a width that is greater than a width at an end portion adjacent to each of the upper and lower spines.

The outer shell can also have other configurations. In one embodiment, the size of the outer shell can vary, for example a diameter of the outer shell can decrease from a proximal end thereof to a distal end thereof. In other aspects, an inner surface of each of the upper and lower spines can include a mating feature formed therein and configured to non-fixedly retain the divider. In another embodiment, each of the upper and lower spines has a width at a proximal end thereof that is greater than a width at a distal end thereof.

Method of manufacturing a medical device are also provided, and in one embodiment the method includes injection molding a substantially cylindrical monolithic outer shell such that the outer shell has an inner lumen extending therethrough, and a plurality of ribs spaced longitudinally along the outer shell and extending partially circumferentially around the outer shell with elongate slots separating each rib. The method further includes injection molding a divider having a height greater than a width. A divider is then advanced into the inner lumen of the outer shell such that the divider separates the inner lumen into first and second elongate channels, the divider being freely slidable relative to the shell. The method can further include mating a proximal end of the outer shell to a distal end of an elongate shaft, and mating a distal end of the outer shell to a proximal end of an end effector. A first articulation band can be advanced through the elongate shaft and through the first elongate channel, and a second articulation band can be advanced through the elongate shaft and through the second elongate channel. The first and second articulation bands can be freely longitudinally slidable within the first and second elongate channels. The method can also include mating the first and second articulation bands to opposed sides of the end effector. In one embodiment, the first and second articulation bands can each be advanced into a channel formed in an inner sidewall of the outer shell.

In one embodiment, injection molding the divider can comprise injection molding first and second dividers, each having a height greater than a width. The method can also include advancing a knife through a first pathway formed between the first and second dividers, and advancing an actuation band through a second pathway formed between the first and second dividers. The method can also include advancing a conducting member through a plurality of longitudinally spaced brackets formed on an external surface of the first divider.

The outer shell can be injection molded to have a variety of configurations. In one embodiment, outer shell has an upper spine and a lower spine, each extending along at least a portion of a length of the outer shell. The plurality of spaced arcuate ribs can include a first plurality of spaced arcuate ribs extending between the upper and lower spines along a first side of the outer shell, and a second plurality of spaced arcuate ribs extending between the upper and lower spines along a second side of the outer shell.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
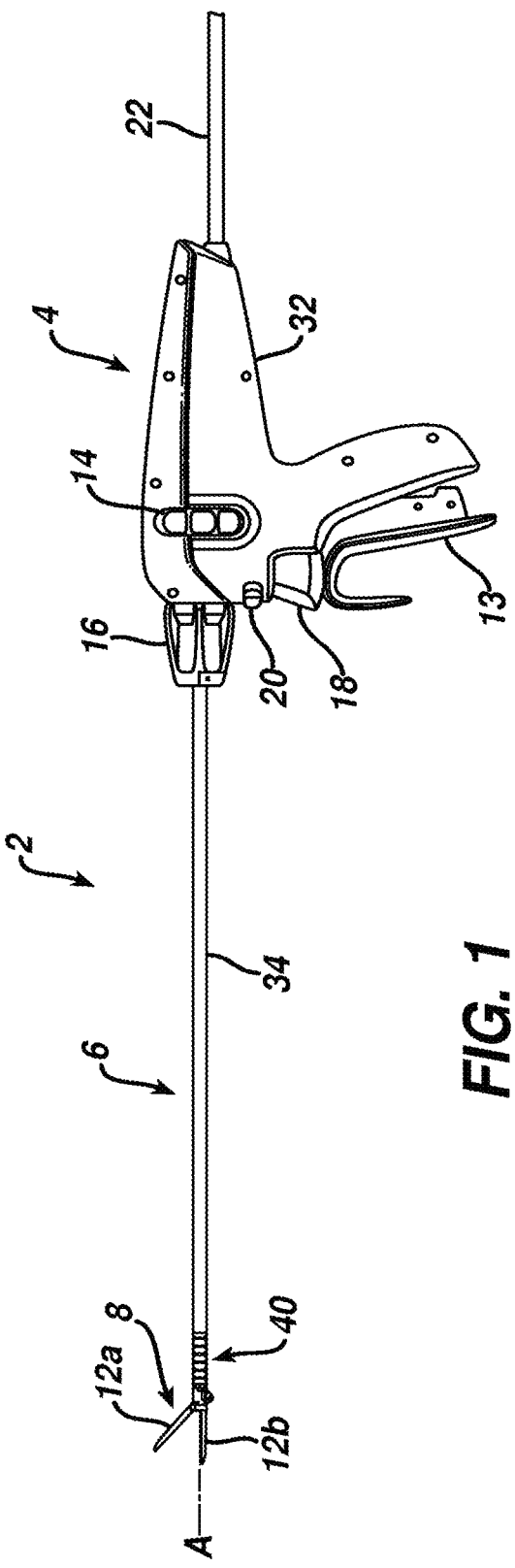
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for allowing articulation of an end effector on a surgical instrument are provided. In general, a surgical device is provided that includes an elongate shaft having a flexible neck portion extending along a length thereof. The flexible neck portion includes a monolithic outer shell having an inner lumen extending therethrough, and at least one flexible divider that is separate from the outer shell and that is disposed within and extends through the inner lumen of the shell such that the divider separates the inner lumen into at least first and second elongate channels. The divider is disposed within the shell so that it is freely longitudinally slidable relative to the outer shell while being constrained from moving away from a longitudinal axis of the outer shell. The first and second elongate channels formed in the inner lumen of the shell can receive first and second articulation members, respectively. The first and second articulation members can translate axially within the outer shell while being prevented from moving towards the longitudinal axis of the shell. The surgical device can also include an end effector that is coupled to a distal end of the elongate shaft, e.g., to a distal end of the flexible neck portion of the elongate shaft, and that is coupled to the first and second articulation members.

In use, axial translation of the articulation members within the first and second elongate channels is effective to cause the flexible neck to bend, thereby causing articulating movement of the end effector. The divider can provide lateral support of the articulation members increasing rigidity of the flexible portion and it can provide support to the shell to prevent collapse of the shell during use of the surgical device. The use of a separate divider is also advantageous as it allows the shell to be manufactured as a single, monolithic structure with the divider being slidably disposed therein. Such a configuration can significantly reduce manufacturing costs without sacrificing the ability to allow for precisely controlled articulation of an end effector on a surgical device. Furthermore, an advantage of a monolithic outer shell with separate dividers slidably disposed therein is that the flexible portion can have a reduced length as compared to conventional articulating portions, while having a proper bending angle. The shorter flexible portion can allow a surgical device to access smaller and/or narrower spaces within a patient's body.

Figure 2:
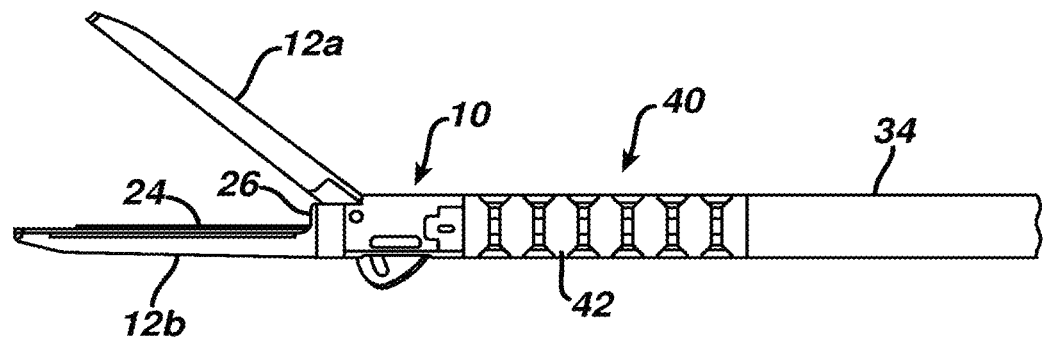
FIG. 2 is a side view of a distal portion of the surgical device of FIG. 1, with the jaws shown in an open position.
Figure 3:
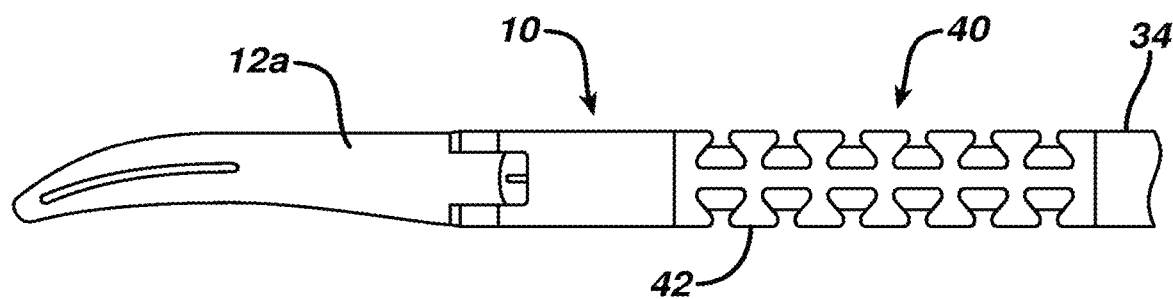
FIG. 3 is a top view of a distal portion of the surgical device of FIG. 1, with the jaws shown in a closed position.

FIGS. 1-3 illustrate one embodiment of a surgical device 2 having a proximal handle portion 4 with a shaft assembly 6 extending distally therefrom, and a working element, referred to herein as an end effector 8, that is coupled to a distal end of the shaft assembly 6. The end effector 8 can be coupled to the shaft assembly 6 at a pivot joint 10. The end effector 8 can have a variety of sizes, shapes, and configurations. As shown in FIGS. 1-3, the end effector 8 is disposed at a distal end of the surgical device 2 and has first and second opposed jaws 12a, 12b. The end effector 8 in the illustrated embodiment is in the form of a tissue grasper having a pair of opposed jaws 12a, 12b configured to move between open and closed positions. The first top or upper jaw 12a and the second bottom or lower jaw 12b can be pivotally connected together at the pivot joint 10. One or both of the jaws 12a, 12b can include electrodes 24, which can be configured to contact tissue positioned between the jaws 12a, 12b and to apply energy thereto. The electrodes 24 are arranged longitudinally along the lower jaw 12b in the illustrated embodiment, but the electrodes 24 can be arranged in any of a variety of ways on the upper jaw 12a and/or the lower jaw 12b.

It should be appreciated that the surgical device 2 having the handle portion 4 is described herein by way of example only, and that the device need not include a handle. The embodiments disclosed herein can be used in a robotic system in which the shaft assembly and the end effector can be coupled to a robotic arm that is manipulated by a robotic control system. A person skilled in the art will also appreciate that the embodiments disclosed herein can be used in connection with any surgical end effector, and are not intended to be limited to an end effector having jaws. Other exemplary end effectors include, e.g., scissors, a babcock, a retractor, etc.

The handle portion 4 can have a variety of sizes, shapes, and configurations. For example, as shown in FIG. 1, the handle portion 4 can include a main housing 32, which can house a variety of elements therein and can have some elements accessible outside thereof, such as various actuators configured to effect operation of the surgical device. For example, in the illustrated embodiment, the main housing 32 can house a first actuator 13, a second actuator 14, a third actuator 16, a fourth actuator 18, and a fifth actuator 20 of the handle portion 4.

The first actuator 13 can be configured to effect opening and closing of the opposed jaws 12a, 12b, e.g., movement of the jaws 12a, 12b toward and away from one another. The jaws 12a, 12b are shown in the open position in FIGS. 1 and 2 and in a closed position in FIG. 3. In the illustrated embodiment, the upper jaw 12a can be configured to move relative to the lower jaw 12b, which can remain stationary relative to the shaft assembly 6. In other embodiments, the lower jaw can be configured to move relative to the upper jaw which can remain stationary, or both the upper and lower jaws can move relative to one another.

The second actuator 14 can be configured to effect articulation of the end effector 8, e.g., movement of both jaws 12a, 12b in a same direction relative to a longitudinal axis A of the shaft assembly 6. The articulation can be independent of the opening and closing of the jaws 12a, 12b, which can occur with the end effector in any articulated position. The end effector 8 is shown in an unarticulated position, e.g., at a zero angle relative to the longitudinal axis A, in FIGS. 1-3.

The third actuator 16 can be configured to rotate the shaft assembly 6 with the end effector 8 about the longitudinal axis A of the shaft assembly 6. The fourth actuator 18 can be configured to fire the device, e.g., by causing a cutting element 26 (e.g., a knife, a blade, etc.) to translate through the end effector 8.

As in this illustrated embodiment, the surgical device 2 can be powered and it can be configured as an electrosurgical tool that applies energy to tissue, such as radiofrequency (RF) energy. The handle portion 4 can have a power cord 22 extending proximally therefrom that can be configured to supply electrical power to the surgical device 2, such as by connecting to a generator, by plugging into an electrical outlet, etc. The fifth actuator 20 can be configured to turn on and off the application of the energy, which can be delivered to tissue via the electrodes 24.

As mentioned above, the handle portion 4 is described by way of example only. The surgical device described herein can include a different handle or a control mechanism other than a handle, as the described techniques are not limited to a specific mechanism used to operate the device.

The shaft assembly 6 can have a variety of sizes, shapes, and configurations. The shaft assembly 6 can have any longitudinal length, and in an exemplary embodiment it can have a length that allows the handle portion 4 to be manipulated outside a patient's body while the shaft assembly 6 extends through an opening in the body with the end effector 8 disposed within a body cavity. By way of non-limiting example, the length can be in the range of about 20 cm to 40 cm, e.g., about 33 cm. In this way, the end effector 8 can be easily manipulated when the surgical device 2 is in use during a surgical procedure. The shaft assembly 6 can have any diameter. For example, the shaft assembly's diameter can be less than or equal to about 15 mm, e.g., less than or equal to about 10 mm, less than or equal to about 7 mm, less than or equal to about 5 mm, etc., which can allow for insertion of the shaft assembly 6 through an minimally invasive access device, such as during a laparoscopic surgical procedure. The end effector 8 mated to the shaft assembly's distal end can have a diameter equal to or less than the shaft assembly's diameter, at least when the jaws 12a, 12b are in the closed position, which can facilitate insertion of the device's distal portion into a patient's body.

As shown in FIGS. 1-3, the shaft assembly 6 of the surgical device 2 includes an elongate shaft portion or elongate shaft 34 and a flexible neck portion 40 extending between the elongate shaft 34 and a proximal end of the end effector 8. The flexible neck 40 can receive therein actuating members passing therethrough so that operation of the actuating members causes the flexible neck 40 to articulate. Thus, the flexible neck 40 can bend so as to allow articulating movement of the end effector 8 in a direction transverse to the longitudinal axis A of the elongate shaft 34, as discussed in more detail below. The flexible neck 40 can flex in opposite directions (e.g., right and left) with respect to the longitudinal axis of the elongate shaft 34. In an exemplary embodiment, the flexible neck 40 is limited to articulation in a single plane.

The flexible neck 40 can be coupled to the end effector 8 and the elongate shaft 34 in any suitable manner, as embodiments are not limited in this respect. Furthermore, although in the illustrated embodiment the flexible neck 40 is coupled distal of and adjacent to the elongate shaft 34, it should be appreciated that the flexible neck 40 can be positioned more proximally along the shaft assembly.

As shown in FIGS. 2, 3, 4A, and 4B, the flexible neck 40 can be in the form of an elongate flexible substantially cylindrical monolithic outer shell 42 having an inner lumen 44 extending therethrough. The outer shell 42 can be sufficiently flexible so as to flex or bend without cracking, breaking, or otherwise becoming damaged, which can facilitate articulation of the end effector 8. The inner lumen 44 is configured to receive at least one flexible divider 46 that can be separate from the outer shell 42 and that can be slidably disposed within the outer shell 42. The at least one divider 46 can be configured to be disposed within the inner lumen 44 so as to separate the inner lumen 44 into elongate channels or pathways, as discussed in more detail below.

In the illustrated embodiment, the at least one divider 46 includes a first divider 46a and a second divider 46b that are configured to be retained within the outer shell 42 while being freely longitudinally slidable relative to the outer shell 42. The outer shell 42 and the first and second dividers 46a, 46b can flex so that the entire flexible neck 40 can bend transverse to a longitudinal axis of the elongate shaft 34 to thereby allow the end effector coupled distally thereto to articulate, as will be discussed in more detail below. The first and second dividers 46a, 46b can provide rigidity to the outer shell 42 while at the same time allowing the outer shell 42 to bend. Furthermore, the first and second dividers 46a, 46b can support multiple actuating elements within the outer shell 42. In the illustrated embodiment, the first and second dividers 46a, 46b separate the inner lumen 44 into channels that receive first and second articulation members, a cutting element (e.g., a knife), an actuation band coupled to the end effector 8 for opening and closing the first and second jaws, and a conductor.

As shown in FIGS. 4A-4D, the outer shell 42 can be a substantially cylindrical monolithic component having an inner lumen 44 extending therethrough. The outer shell 42 defines a longitudinal axis A extending between a proximal end 42p thereof and a distal end 42d thereof. When the flexible neck 40 is in a non-bent configuration, the longitudinal axis of the outer shell 42 can coincide and be co-axial with the longitudinal axis of the elongate shaft 34. As shown, the outer shell 42 can have a substantially circular cross-section. However, the cross-section can have an oval, octagonal or other shape. A diameter of the outer shell 42 can be substantially constant throughout a length thereof. However, in some embodiments, the diameter of the outer shell 42 can decrease from the proximal end 42p to the distal end 42d. In one embodiment, the diameter of the outer shell 42 can be about 5 mm. However, the outer shell 42 can have any suitable diameter (e.g., equal or greater than about 5 mm, or equal or less than about 5 mm). For example, in some embodiments, the diameter of the outer shell 42 can be about 10 mm.

Figure 4A:
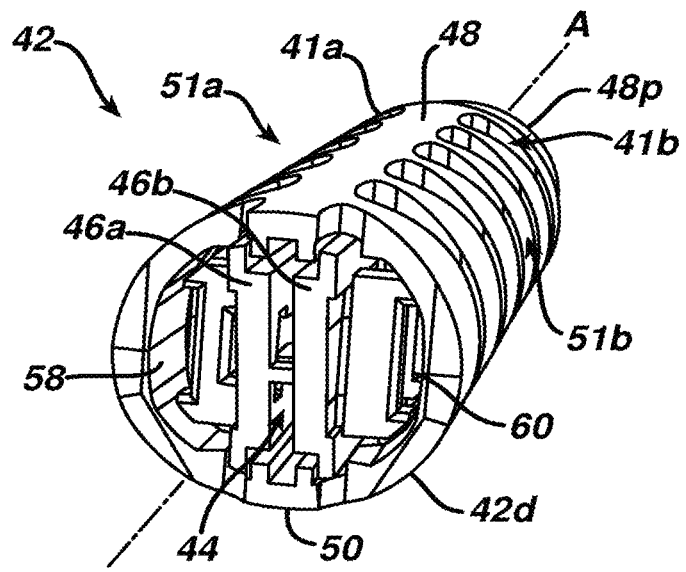
FIG. 4A is a perspective view of a flexible portion of the surgical device of FIG. 1 with a knife, first and second articulation bands, and an actuating band removed.
Figure 4B:
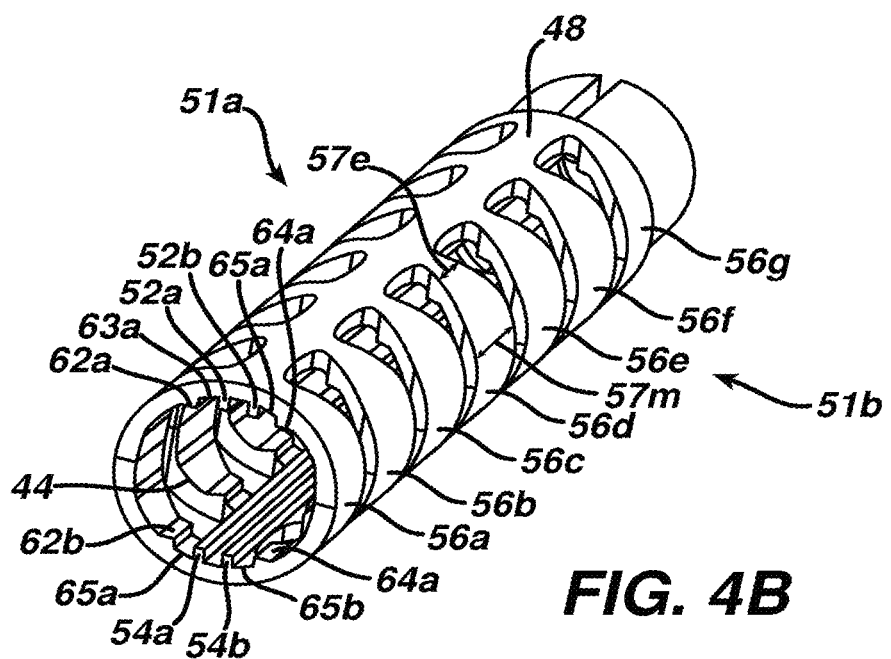
FIG. 4B is a perspective view of an outer shell of the flexible portion of FIG. 4A.

As further shown in FIGS. 4A-4D, the outer shell 42 can include two rows of slots formed in opposite sides thereof that define first and second opposed longitudinal spines and first and second rows of arcuate ribs extending between the spines along a circumference of the outer shell 42. In particular, the outer shell 42 can include an upper spine 48 and a lower spine 50 each extending along at least a portion of a length of the outer shell 42 (the lower spine 50 is obscured in FIG. 4A, however an internal surface of the lower spine 50 is shown in FIGS. 4A and 4B). It should be appreciated that the upper and lower spines 48, 50 are referred to herein as "upper" and "lower" for description purposes only, as the surgical device 2 with the flexible neck 40 can be oriented in different ways. For the purposes of this disclosure, the upper spine 48 is disposed on the same side as the upper jaw 12a and the lower spine 50 is disposed on the same side as the lower jaw 12b.

Figure 5:
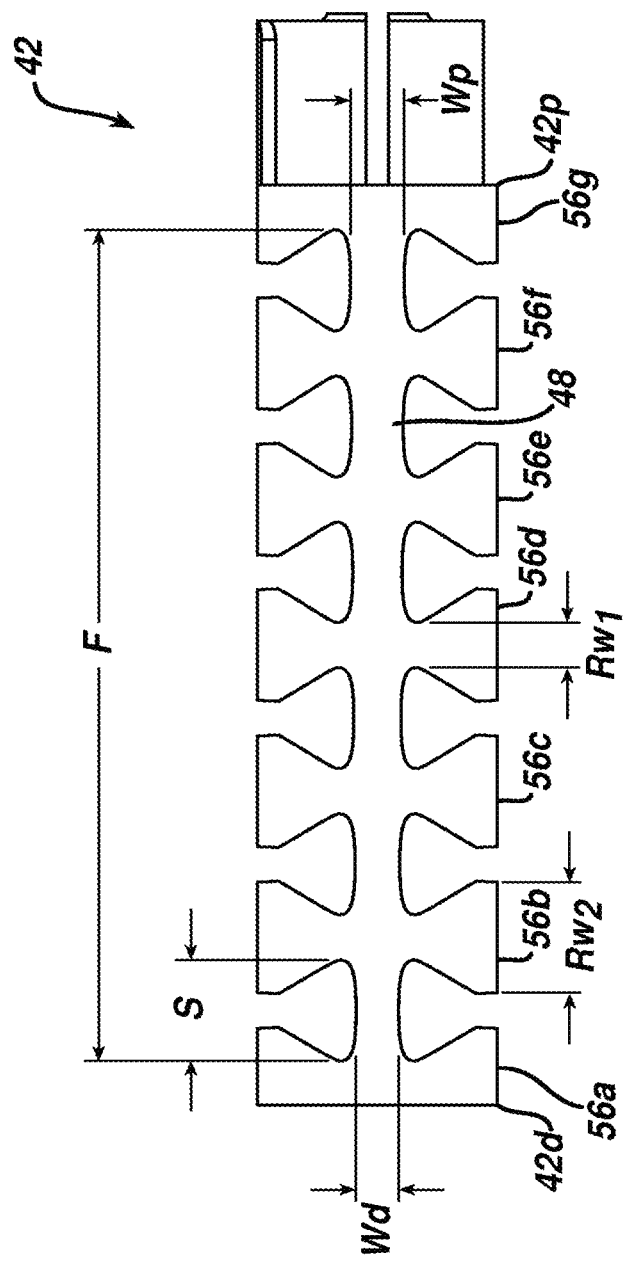
FIG. 5 is a top view of the outer shell of the flexible portion of FIG. 4A.

The upper and lower spines 48, 50 can have any suitable configuration and size. In the illustrated exemplary embodiments, each of the upper and lower spines 48, 50 can have a width at a proximal end thereof that is greater than a width at a distal end thereof. For example, as shown in FIG. 5 for the upper spine 48, a proximal width Wp of the upper spine 48 at the proximal end 48p thereof is greater that a distal width Wd of the upper spine 48 at the distal end 48d thereof. The width of the lower spine 50 can vary in a similar manner. The widths Wd, Wp can have any suitable values. For example, in one embodiment, the distal width Wd can be about 0.038 inches and the proximal width Wp can be about 0.048 inches. In some embodiments, the width of the upper and lower spines 48, 50 can taper distally so that the proximal width Wp is about 20% greater than the distal width Wd. However, the width at the proximal end of the spine can differ from the width at the distal end of the spine in other manners, for example, with the difference ranging from about 10% to about 50%. Having the spines with a reduced width at a distal end thereof can enhance bending properties of the outer shell and facilitate control of the flexible neck 40. The characteristics can be further improved by the overall configuration of the outer shell 42 having a diameter that reduces from the proximal end of the outer shell 42 toward the distal end thereof.

A person skilled in the art will appreciate that the widths of the upper and lower spines 48, 50 can reduce gradually towards the distal ends thereof, or can vary in any other manner. In the illustrated embodiment, the widths of the upper and lower spines 48, 50 can be substantially identical. However, in other embodiments, the upper and lower spines 48, 50 can have different widths that can vary along a length of the outer shell 42 in any suitable manner.

Figure 4C:
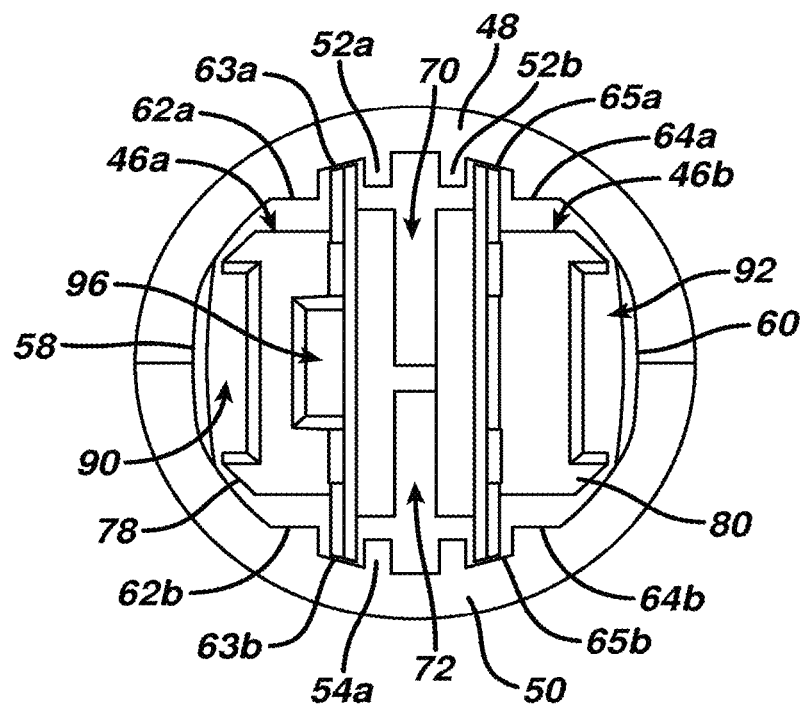
FIG. 4C is an end view of the outer shell of FIG. 4A having first and second dividers extending therethrough.
Figure 4D:
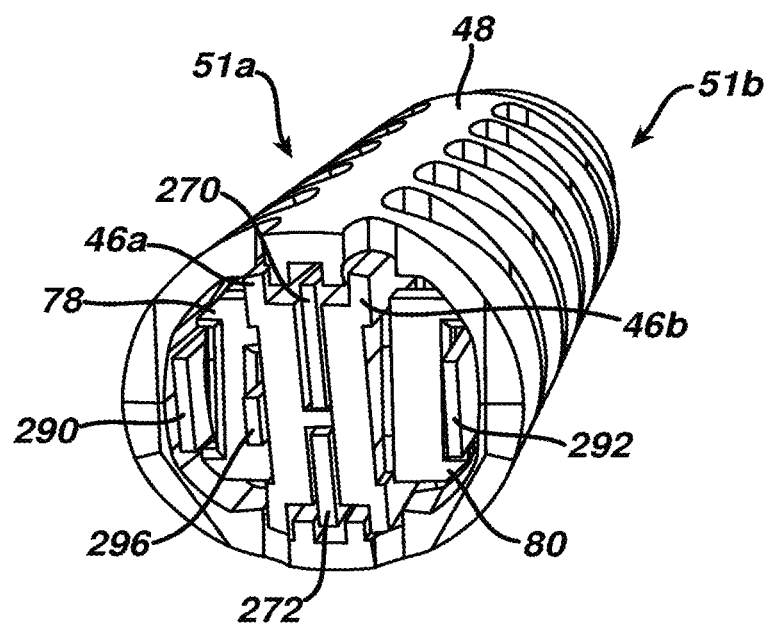
FIG. 4D is a perspective view of the flexible portion of FIG. 4A with the knife, articulation bands, and actuation band extending therethrough.

As further shown in FIGS. 4A, 4B, and 4D, the outer shell 42 can include a first series of arcuate ribs 51a disposed along one side of the outer shell 42 and a second series of arcuate ribs 51b disposed along another side of the outer shell 42 (an inner surface of the first series of arcuate ribs is shown in FIGS. 4A and 4B). In the illustrated embodiment, as shown in FIG. 4B, the second series of arcuate ribs 51b includes, for example, ribs 56a, 56b, 56c, 56d, 56e, 56f, 56g. The first and second series of arcuate ribs 51a, 51b are spaced apart longitudinally along opposite sides of the outer shell 42 and each rib extends between the upper and lower spines 48, 50 at least partially around the circumference of the outer shell 42. As shown, the first and second arcuate ribs 51a, 51b are spaced apart so as to form elongate slots therebetween that are also spaced longitudinally along a length of the outer shell. In particular, first elongate slots 41a are formed between ribs of the first series of arcuate ribs 51a, and second elongate slots 41b are formed between ribs of the second series of arcuate ribs 51b. The shape and size of the elongate slots are complementary to the shape and size of the ribs.

As shown, rib 56a positioned at the distal end 42d of the outer shell 42 and rib 56g positioned at the proximal end 42p of the outer shell 42 have a width that is half of a width of ribs 56b, 56c, 56d, 56e, 56f. As shown in FIG. 5, which illustrates a side view of the outer shell 42, the ribs of the outer shell 42 can be described as flexible segments S, each extending longitudinally along opposite sides of an elongate slot formed between adjacent ribs. A length F of the outer shell along which the outer shell can bend (so-called "flexible length") can be defined between a distal-most end of the distal-most elongate slot and a proximal-most end of the proximal-most elongate slot. Thus, the total length of the flexible neck 40 can be defined as a sum of the flexible length F and a length of the spine along the distal-most and proximal-most ribs.

The first and second series of arcuate ribs 51a, 51b can have any suitable configuration and dimensions. For example, the width of each rib can vary. In the illustrated embodiment, each of the first and second series of arcuate ribs 51a, 51b has a mid-portion Wm with a width that is greater than a width at an end portion We adjacent to each of the upper and lower spines 48, 50, as shown by way of example in FIG. 4B for the rib 56d. The end portion We of the rib 56d in FIG. 4B is adjacent the upper spine 48, and an end portion of the rib 56d adjacent the lower spine 50 (not shown) has the same or substantially the same width as end portion We. Others ribs of the first and second series of arcuate ribs 51a, 51b are configured similarly.

The width of each of the spaced ribs can gradually increase from the end portion to the mid-portion and then gradually decrease from the mid-portion to the end portion. It should be appreciated, however, that, in other embodiments, each of the first and second arcuate ribs 51a, 51b can have a constant width along an entire length thereof. In yet other embodiments, the width of the ribs can vary in other ways.

The width of the ribs can vary along their length based on the required strength and resiliency of the outer shell to support articulation bands while preventing their buckling, and on a desired articulation angle. Variation in the width of the ribs from a location near the spine to a location away from the spine can contribute to the ability of the flexible portion to prevent articulation members from buckling and can reduce a possibility of undesired excessive articulation of the flexible portion. In addition, the width of the ribs can be selected so as to maintain a smooth arcuate shape of each rib during articulation of the flexible neck. In one embodiment, the width of the ribs, as measured across the end portion We and across the mid-portion Wm (FIG. 4B), shown as Rw1 and Rw2, respectively, in FIG. 5, can be about 2.3 mm. In some embodiments, the width of the ribs can vary along their length from about 0.7 mm to about 3.2 mm. In other embodiments, the width can vary along their length from about 1.6 mm to about 3.5 mm. In other embodiments, the width of the ribs can vary along their length from about 1.4 mm to about 6.4 mm. In yet other embodiments, the width of the ribs can vary along their length from about 3.2 mm to about 7.0 mm. For example, in embodiments in which a diameter of the outer shell is about 5 mm, the width of the ribs can vary along their length from about 1.5 mm to about 3.5 mm. As another example, in embodiments in which a diameter of the outer shell is about 10 mm, the width of the ribs can vary along their length from about 3.0 mm to about 7.0 mm.

The width of the distal-most and proximal most ribs 56a, 56g can be about half of the width of the ribs disposed therebetween. One skilled in the art will appreciate that the width of the ribs can be selected from any other suitable range.

The length of the ribs can vary as well. The first and second series of arcuate ribs 51a, 51b can have substantially the same length as measured between the upper and lower spines 48, 50. In embodiments in which the diameter of the outer shell 42 tapers distally, ribs disposed more distally can have a shorter length than ribs disposed more proximally along the length of the outer shell 42. As another variation, a width of one or both of the upper and lower spines 48, 50 can taper distally while the length of the ribs can be the same or substantially the same. One skilled in the art will appreciate that the length of the ribs can vary in other ways as well.

The outer shell 42 can include any suitable number of ribs. Although five full-width ribs and two half-width ribs (forming six flexible segments) are shown in the illustrated embodiment, the outer shell 42 can have any suitable number of ribs and flexible segments. For example, in some embodiments, the number of flexible segments can be four, six, seven, or eight. The described embodiment can allow manufacturing the outer shell having a reduced number of flexible segments as compared to existing devices. For example, the number of the flexible segments can be eight or less. However, in some embodiments, the number of flexible segments can be greater than eight. The number of flexible segments can depend, for example, on a length of the outer shell 42 that is appropriate to achieve a desired articulation angle, while conforming to stress/strain requirements of a material used to manufacture the shell.

As mentioned above, the upper and lower spines 48, 50 of the outer shell 42 can have a width that decreases from the proximal end thereof to the distal end thereof. In some embodiments, if the total length of flexible segments or "flexible length" F (FIG. 5) is defined as x, the width Wp of the spine at the proximal end thereof can be defined as 0.080x, and the width Wd of the spine at the distal end thereof can be defined as 0.064x. The width of the upper and lower spines 48, 50 can be substantially the same or it can be different.

Referring back to FIGS. 4A and 4B, external surfaces of the first and second series of arcuate ribs 51a, 51b can be substantially smooth and free of surface features. The internal surfaces of the first and second series of arcuate ribs 51a, 51b, on the other hand, can include various surface features. For example, as shown in FIGS. 4A and 4B, the internal surface of each of the first arcuate ribs 51a can include a recess or cut-out 58 (shown in FIGS. 4A and 4B) configured to seat a first articulation member. Similarly, the internal surface of each of the second arcuate ribs 51b can include a recess or cut-out 60 configured to seat a second articulation member. The cut-outs 58, 60 can be formed so as to face each other across the inner lumen 44, and each cut-out 58, 60 can define an elongate channel that slidably seats an articulation member. In this way, the first and second articulation members can be disposed in the cut-outs between the inner surfaces of the ribs and external surfaces of the dividers 46a, 46b opposite to each other across the inner lumen 44 in a manner that prevents buckling of the first and second articulation members, as discussed in more detail below.

Continuing to refer to FIGS. 4A-4D, walls of the inner lumen 44 formed in the outer shell 42 can include features configured to slidably receive and non-fixedly retain the divider 46 within the inner lumen 44. The features can have any suitable configuration. In the illustrated embodiment, the inner lumen 44 can include longitudinal grooves or tracks each formed between two longitudinal protrusions and configured to seat therein the first and second dividers 46a, 46b. The longitudinal grooves can be formed in the inner lumen 44 so as to extend at least partially therethrough.

As shown in FIGS. 4A-4D, the inner surface of each of the upper and lower spines 48, 50 can include various longitudinal ribs or protrusions spaced apart from each other and defining channels or pathways formed therethrough for seating the divider. By way of example, a first pair of longitudinal upper protrusions 52a, 52b can be formed in the upper spine 48 and a second pair of longitudinal lower protrusions 54a, 54b can be formed in the lower spine 50. Protrusions 52a, 54b can be formed so that they are disposed opposite to each other across the inner lumen 44 of the outer shell 42. In a similar manner, protrusions 52b, 54b are disposed opposite to each other across the inner lumen 44 of the outer shell 42. The protrusions 52a, 52b, 54a, 54b can extend along any length of the flexible neck, but preferably the protrusions extend along substantially the entire length thereof.

As also shown in FIGS. 4C and 4D, the internal surfaces of the arcuate ribs 51a, 51b can include third and fourth pairs of longitudinal protrusions 62a, 62b, 64a, 64b formed adjacent to the first and second pairs of protrusions 52a, 52b, 54a, 54b. In particular, the internal surfaces of the first series of arcuate ribs 51a can include upper and lower protrusions 62a, 62b, and the internal surfaces of the second series of arcuate ribs 51b include upper and lower protrusions 64a, 64b. As a result, elongate channels or grooves are defined between the protrusions first, second, third and fourth pairs of protrusions, with the channels or grooves extending along a substantial length of the flexible neck. As shown, two grooves 63a, 65a are formed in the upper spine 48, with a first groove 63a is formed between protrusion 62a and protrusion 52a, and a second groove 65a formed between protrusion 64a and protrusion 52b. Similarly, two additional grooves 63b, 65b are formed in the lower spine 50, with a third groove 63b formed between protrusion 62b and protrusion 54a, and a fifth groove 65b formed between protrusion 64b and protrusion 54b. Grooves 63a, 63b are configured to seat a top and a bottom of the first divider 46a, and grooves 65a, 65b are configured to seat a top and a bottom of the second divider 46b. The grooves thus function to prevent lateral movement of the dividers, e.g., to prevent movement toward and away from the longitudinal axis.

As shown, the inner surface of the ribs between upper protrusions 62a, 64a and upper protrusions 52a, 52b, and the inner surface of the ribs between lower protrusions 62b, 64b and lower protrusions 54a, 54b can be slanted to correspond to the overall cylindrical shape of the outer shell 42. One skilled in the art will appreciate that other surface features can be formed within the inner lumen 44 to slidably receive and non-fixedly maintain therein the at least one divider 46.

In the illustrated embodiment, as shown in FIGS. 4A-4D, protrusions 52a, 62a, 54a, 62b can be disposed on one side of the longitudinal axis A of the outer shell 42 whereas the protrusions 52b, 64a, 54b, 64b can be disposed on another side of the longitudinal axis A. In this way, grooves 63a, 63b seat the first divider 46*a* at a predetermined distance apart along a length of the outer shell 42 from the second divider 46*b*, which is seated in grooves 65*a*, 65*b*.

Figure 6A:
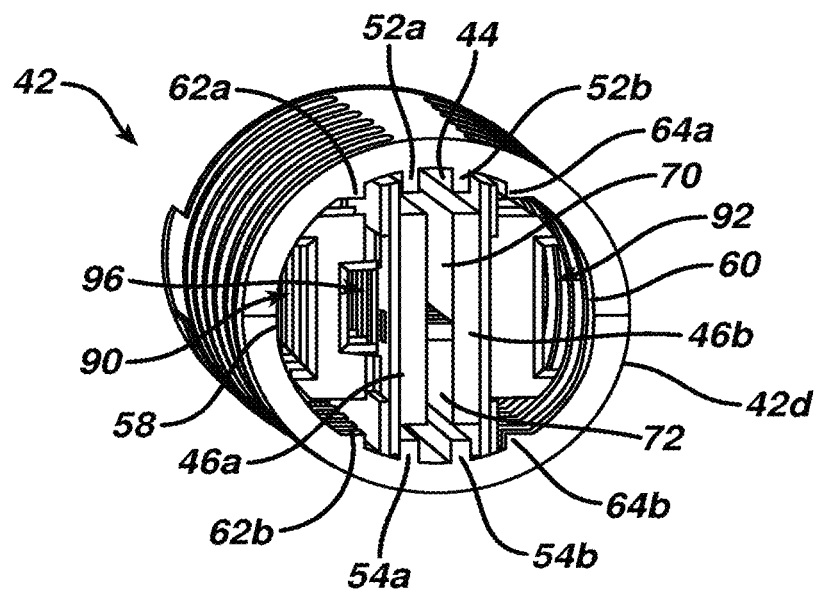
FIG. 6A is a perspective view of a flexible portion of the surgical device of FIG. 1.

FIGS. 6A-6E illustrate the at least one divider 46 that is disposed within the outer shell 42. In the illustrated embodiment, the at least one divider 46 includes first and second flexible dividers 46*a*, 46*b* disposed in the inner lumen 44 of the outer shell 42. The first and second dividers 46*a*, 46*b* are separate components from the outer shell 42 and extend through the inner lumen 44 such that they separate or "divide" the inner lumen 44 into elongate channels or pathways. Thus, as shown in FIG. 6A, the first and second dividers 46*a*, 46*b* define at least first and second outer channels 90, 92 formed on opposed outer sides thereof, and first and second inner channels 70, 72 formed therebetween.

Figure 6B:
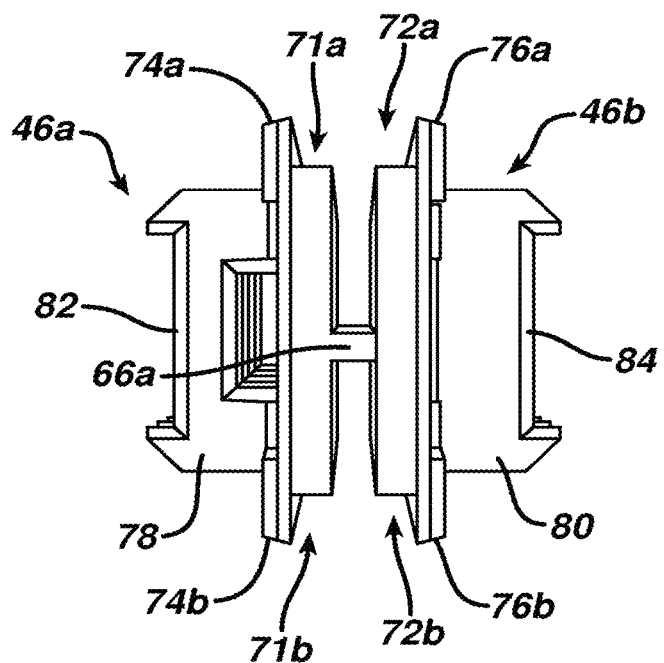
FIG. 6B is an end view of a divider of the flexible portion of FIG. 6A.
Figure 6C:
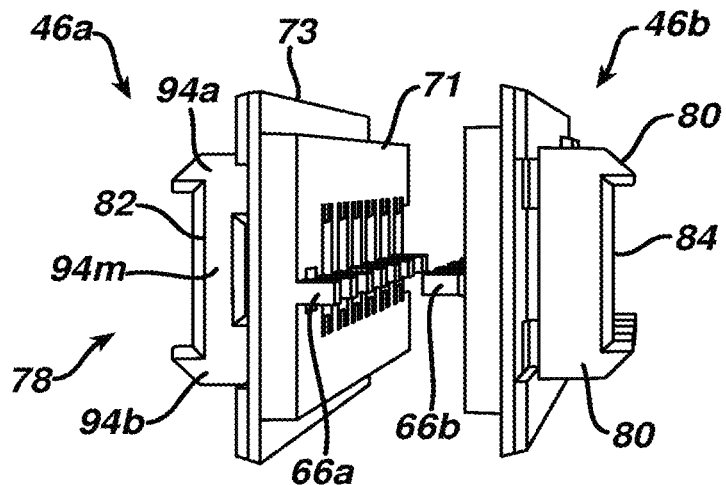
FIG. 6C is a perspective view of the divider of FIG. 6B.
Figure 6D:
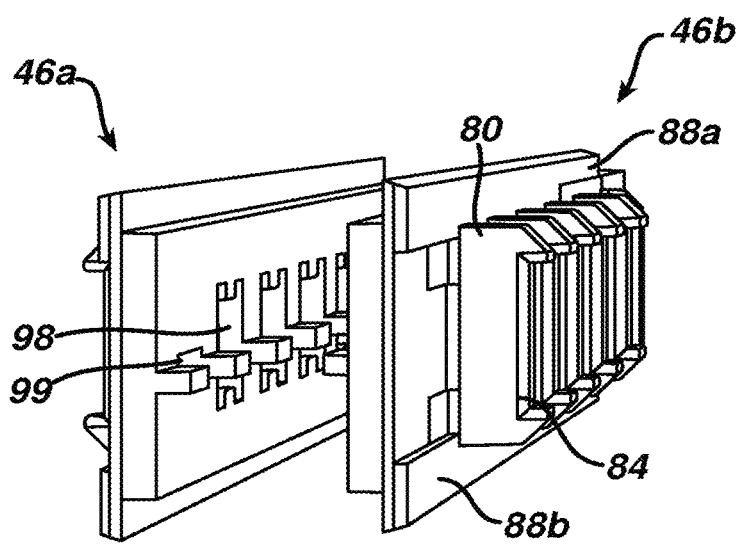
FIG. 6D is another perspective view of the divider of FIG. 6B.
Figure 6E:
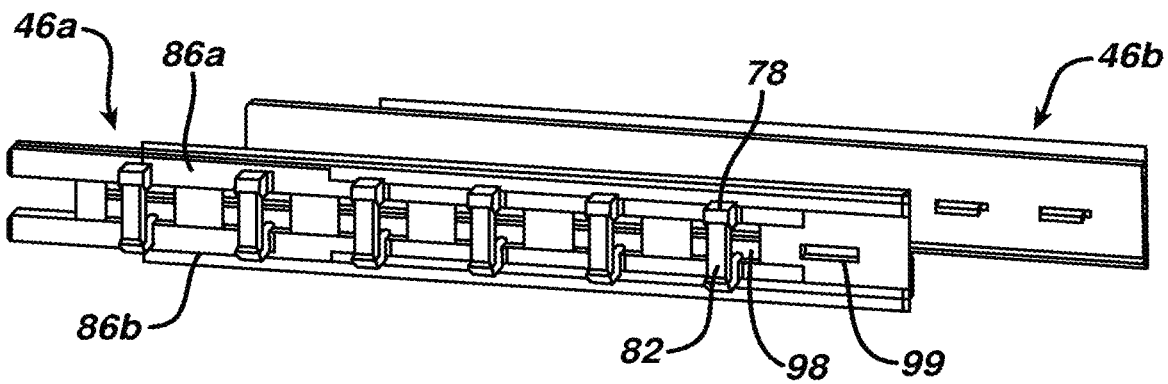
FIG. 6E is another perspective view of the divider of FIG. 6B.

The first and second flexible dividers 46*a*, 46*b* can have any suitable configuration. As shown in FIGS. 6C-6E, the first and second flexible dividers 46*a*, 46*b* can have a generally elongate shape so that they extend through the entire inner lumen 44 or at least a portion thereof. Each of the first and second dividers 46*a*, 46*b* can have a height that is greater than a width. Such a configuration will allow the dividers to bend in a first plane while preventing bending in a second, perpendicular plane. In particular, the relatively narrow width allows the dividers to bend along the length. The first and second dividers 46*a*, 46*b* can be disposed within the inner lumen 44 between the upper and lower spines 48, 50 at a predetermined distance from each other so as to define the elongate channels or pathways on opposite outer sides of the divider and between the inner surfaces of the first and second flexible dividers 46*a*, 46*b*.

The first and second flexible dividers 46*a*, 46*b* can have various features. In the illustrated embodiment, the first and second dividers 46*a*, 46*b* are maintained at a predetermined distance apart via spacers formed on inner surfaces thereof. As shown in FIGS. 6A-6D, the first divider 46*a* has a first protrusion 66*a* and the second divider 46*b* has a second protrusion 66*b*, which are together configured to maintain the first and second dividers 46*a*, 46*b* at a predetermined distance apart along their lengths. The first and second protrusions 66*a*, 66*b* can extend longitudinally along a portion or the entire length of the dividers, and each protrusion 66*a*, 66*b* can be positioned at an approximate midpoint along a height of each of the first and second dividers 46*a*, 46*b*. A person skilled in the art will appreciate that the first and second protrusions 66*a*, 66*b* can be positioned at other locations along the inner surfaces of the dividers.

A shown in FIGS. 6C-6E, the first protrusion 66*a* formed on the inner surface of first divider 46*a* and the second protrusion 66*b* formed on the inner surface of the second divider 46*b* can each be the form of multiple protrusions. The multiple protrusions can have similar configurations or, in some embodiments, they can be different. Furthermore, the size and shape of the protrusions can be substantially similar along the length of one or both of the dividers 46*a*, 46*b*. Alternatively, one or more of the protrusions (e.g., those formed at one or both of the proximal and distal ends of the dividers) can be different from other protrusions. In the illustrated embodiment, the first and second protrusions 66*a*, 66*b* can be alternatingly formed on the inner surfaces of the first and second dividers 46*a*, 46*b* so that a protrusion formed on one of the dividers 46*a*, 46*b* abuts against an inner surface of the other one of the dividers 46*a*, 46*b* in a space between protrusions formed on that other divider. Arranged in this way, the multiple first and second protrusions 66*a*, 66*b* maintain the first and second dividers 46*a*, 46*b* a distance apart while allowing movement of the first and second dividers 46*a*, 46*b* with respect to each other. As one skilled in the art will appreciate, the first and second dividers 46*a*, 46*b* can additionally or alternatively include other feature(s) that maintain the first and second dividers 46*a*, 46*b* a distance apart and allow the dividers 46*a*, 46*b* to flex within the outer shell during operation of the surgical device.

In the illustrated embodiment, the first and second dividers 46*a*, 46*b* can be configured to be non-fixedly retained within the outer shell 42. The first and second dividers 46*a*, 46*b* can be retained within the outer shell 42 so that they can be freely longitudinally slidable relative to the outer shell 42, while being constrained from moving toward or away from the longitudinal axis A of the outer shell 42. The first and second dividers 46*a*, 46*b* can have features configured to retain them within the outer shell 42 in this manner.

As shown in FIGS. 6A-6D, the first and second dividers 46*a*, 46*b* can have top and bottom recesses or stepped surfaces on upper and lower inner surfaces thereof that are configured to be seated on respective surface features formed in internal surfaces of the upper and lower spines 48, 50. Thus, the first divider 46*a* has top and bottom recesses 71*a*, 71*b*, and the second divider 46*b* has top and bottom recesses 72*a*, 72*b*. The recesses can be formed so that each of the dividers has an external wall and an internal wall, the external wall having a greater height than an internal wall. In particular, the top and bottom portions of the external wall protrude beyond the inner wall on both top and bottom sides of the inner wall. The external and internal walls have upper and lower longitudinal surfaces, with the upper and lower longitudinal surfaces of the internal wall being offset from the upper and lower longitudinal surfaces of the external wall. The upper and lower surfaces of the external wall are configured to seat against the inner surface of the respective spine and between the protrusions, as discussed below. It should be appreciated that the external and internal walls can be parts of the same monolithic divider, or they can be manufactured separately and assembled together.

As shown in FIGS. 6A-6D, the first divider 46*a* can have an upper surface 74*a* configured to be seated against the inner surface of the outer shell 42 within the channel defined between upper protrusion 62*a* and upper protrusion 52*a*. The lower surface 74*b* of the first divider 46*a* can be configured to be seated against the inner surface of the outer shell 42 within the channel defined between lower protrusion 62*b* and lower protrusion 54*a*. As mentioned above, the inner surface of the outer shell 42 between the stepped protrusions formed on the ribs and the longitudinal protrusions formed in the spines can be slanted and/or least partially arcuate. Accordingly, as shown, for example, in FIGS. 6A and 6B, the upper and lower surfaces 74*a*, 74*b* of the first divider 46*a* can have a complimentary slanted shape and/or at least partially arcuate shape. The upper and lower surfaces 76*a*, 76*b* of the second divider 46*b* can be shaped similarly. The width of the upper and lower surfaces of the external walls of the dividers can be such that the dividers fit within the channel defined between the protrusions.

As discussed above, the first and second dividers 46*a*, 46*b* are disposed within the outer shell 42 so as to define multiple passageways or channels extending along a length of the outer shell 42. First and second channels can be defined between the inner surfaces of the first and second dividers 46*a*, 46*b* such that the first inner channel 70 is formed above the first and second spacers 66*a*, 66*b* and the second inner channel 72 is formed below the first and second spacers 66*a*, 66*b*.

In the illustrated embodiment, the first and second dividers 46*a*, 46*b* can also include spaced first and second brackets 78, 80, respectively, formed on the external surface thereof. As shown, the brackets 78, 80 are spaced from one another along a longitudinal length of the divider. Each of the first and second brackets 78, 80 includes a cut-out or recess for receiving therein a respective articulation member. Thus, as shown in FIGS. 6A, 6B, 6C, and 6E, each of the first brackets 78 includes a cut-out 82 configured to seat therein a first articulation member. Each of the second brackets 80 includes a cut-out 84 configured to seat therein a second articulation member, as shown in FIGS. 6A, 6B, 6C, and 6D. The cut-outs 82, 84 can have a substantially rectangular shape or any other suitable shape. The brackets 78, 80 prevent movement of the first and second articulation members toward the longitudinal axis while allowing free longitudinal sliding movement of the first and second articulation members. In other words, the articulation members are laterally constrained between the brackets and the shell while being freely longitudinally slidable. The articulation members are also constrained from moving up or down relative to the brackets.

The first and second dividers 46a, 46b can have any suitable number of brackets. In the illustrated embodiment, each of the dividers 46a, 46b can include six brackets, as shown by way of example for the divider 46a in FIG. 6E. However, one skilled in the art will appreciate that the first and second dividers 46a, 46b can include any suitable number of brackets or other features configured to slidably support the first and second articulation members within the outer shell while restraining movement of the articulation members in an appropriate manner.

In use, the first articulation member can be seated in the cut-outs 82 in the first brackets 78 so that it sits against the cut-out 58 formed in the internal surface of the first series of arcuate ribs 51a, and the second articulation member can be seated in the cut-outs 84 in the second brackets 80 so that it sits against the cut-outs 60 formed in the internal surface of each of the second series of arcuate ribs 51b (FIG. 6A). In this way, a first outer elongate channel 90 for receiving the first articulation member is defined between the outer surface of the first brackets 78 and the inner surface of the first arcuate ribs 51a, and a second outer elongate channel 92 for receiving the second articulation member is defined between the outer surface of the second brackets 80 and the inner surface of the second arcuate ribs 51b. Thus, the first and second articulation members can be disposed on opposite sides of the longitudinal axis of the outer shell 42 and they can be held tightly but slidably between the brackets 78, 80 and inner surfaces of the ribs. Such a configuration can prevent buckling of the articulation members.

In the illustrated exemplary embodiment, the external walls of the first and second dividers 46a, 46b have longitudinal top panels 86a, 88a extending along a side adjacent to a top of the walls and longitudinal bottom panels 86b, 88b extending along a side adjacent to a bottom of the walls, as shown in FIGS. 6C-6D. Each of the brackets 78, 80 can be formed on a respective one of the dividers 46a, 46b so as to be positioned on and extend between the respective top and bottom panels. However, one skilled in the art will understand that the brackets 78, 80 can be attached to or monolithically formed on the external surfaces of the dividers 46a, 46b in any suitable manner. Regardless of the specific configuration, the brackets 78, 80 can be configured so that the dividers have desired flexibility and resilient elasticity.

In the illustrated embodiment, each first bracket 78 can be disposed on the external surface of the first divider 46a so that top and bottom portions 94a, 94b of the bracket 78 are coupled to the external surface (e.g., to top and bottom panels 86a, 86b, respectively) while a middle portion 94m of the bracket 78 is offset from the external surface. In this way, the first brackets 78 can define a bracket channel 96 (FIG. 6A) extending therethrough. The first bracket channel 96 can receive, for example, an electrically conductive member.

As shown in FIGS. 6D and 6E, the first divider 46a can a generally rectangular cut-out or thru-opening 98 formed in the divider at a location between the ends of one or more of the brackets 78. In the illustrated embodiment, as shown in FIG. 6E, six thru-openings 98 are formed in the divider adjacent to each bracket 78. However, any suitable number of thru-openings 98 can be formed, and the number of cut-outs need not be identical to the number of the brackets 78. The first protrusions 66a formed on an inner side of the first divider 46a can be formed between the thru-openings 98. The openings 98 can have any suitable size and shape. In the illustrated embodiments, the second protrusions 66b formed on an inner side of the second divider 46b can partially extend into the thru-openings 98.

As shown in FIGS. 6D and 6E, the first divider 46a can have an additional cut-out or thru-opening 99 adjacent to the distal end of the outer shell 42. Thru-opening 99 can be smaller is size than the thru-openings 98 adjacent the brackets. In the illustrated embodiments, the thru-openings 99 can partially receive therein an opposite protrusion of the second protrusions 66b. It should be appreciated, however, that, in some embodiments, some or all of the second protrusions 66b formed on the inner side of the second divider 46b do not extend into openings formed in the opposed wall of the first divider 46a.

It should be appreciated that any number of generally rectangular or otherwise shaped openings of a suitable size can be formed. In the illustrated embodiment, the second divider 46b need not include such openings, as shown in FIG. 6E. However, if required by a specific design, in some embodiments, both of the first and second dividers or only one of them can include a suitable number of openings of various shapes and sizes. The openings such as openings 98 and 99, and/or any other openings and features of the dividers can be formed so as to allow manufacturing the dividers using molding.

Although in the illustrated embodiment the second brackets 80 disposed on the external surface of the second divider 46b are not configured to form a pathway extending therethrough, in some embodiments, an additional pathway can be defined by the second brackets 80 as well. As another variation, in some embodiments, the additional pathway can be defined through the second brackets 80 instead.

The first and second brackets 78, 80 and cut-outs 82, 84 formed therein can have a height, width, and length appropriate to seat the first and second articulation members and so as to support the first and second articulation members during their movement within the outer channels 90, 92 (FIG. 6A). As shown in FIG. 6B, the first and second brackets 78, 80 can have substantially the same width. As also shown, the external surfaces of the first and second brackets 78, 80 can be disposed at substantially the same distances from the internal surfaces of the first and second dividers 46a, 46b. As mentioned above, the first and second dividers 46a, 46b can be configured so as to bend at substantially the same angle in both directions thus causing the end effector to articulate in a similar manner.

Figure 6F:
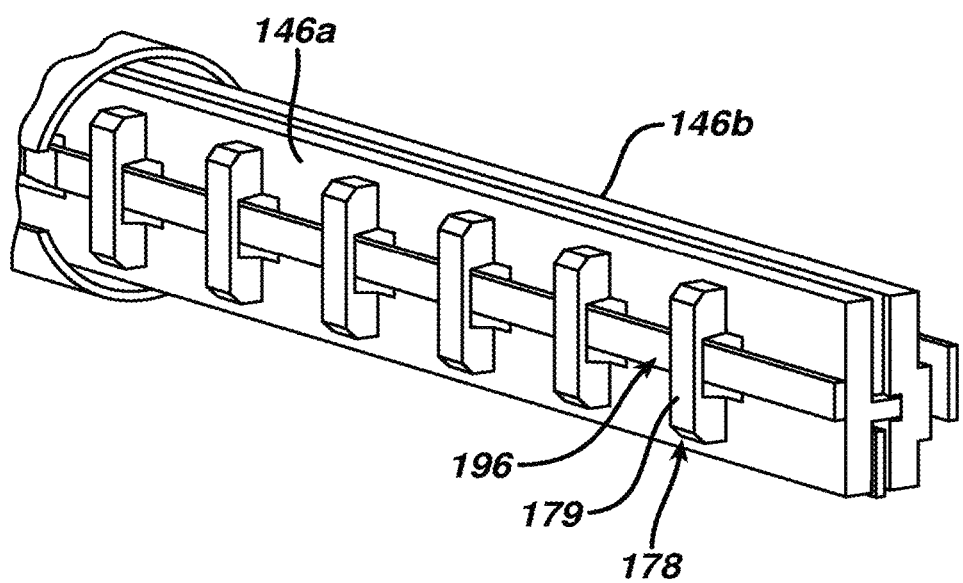
FIG. 6F is a perspective view of another embodiment of a flexible portion of a surgical device with the outer shell removed.

FIG. 6F illustrates another embodiment of a divider 146 that includes first and second dividers 146a, 146b configured to be disposed within an outer shell so as to divide the shell into channels, similarly to the divider 46. However, as FIG. 6F, the first and second dividers 146a, 146b have brackets 178 (shown for the first divider 146a) formed on external surfaces thereof that do not have cut-outs similar to cut-outs 82, 84 formed on the divider 46. Instead, external surfaces 179 of the brackets 178 are substantially flat. Articulation members can be pressed between the external surfaces of the brackets 178 and the internal walls of the outer shell (not shown) which may or may not have cut-outs formed therein. It should be appreciated, however, that the surfaces of the brackets 178 can have any other suitable features.

As also shown in FIG. 6E, the external wall of the first divider 146a can be free of surface features (e.g., panels). However, as one skilled in the art will appreciate, the external wall of the first divider 146a can have any suitable features.

The flexible neck assembly described herein allows articulating movements of an end effector coupled to an elongate shaft of a medical device. When the articulation members passing through the elongate shaft and through the flexible neck are operated so as to cause the flexible neck to bend, e.g., by pulling one of the articulation members proximally while the other is allowing to move distally, the end effector is caused to articulate to the right or to the left relative to the longitudinal axis of the elongate shaft. The flexible neck can be configured such that, when it bends, the outer shell and the first and second dividers non-fixedly disposed therein can slide freely with respect to each other. At the same time, sufficient structural rigidity of the flexible neck and uniform curvature (when articulated) is maintained and the flexible neck supports the actuation shafts (e.g., first and second articulation members) extending therethrough to cause the end effector to articulate at a precise articulation angle. The configuration of the flexible neck allows free longitudinal sliding movement of articulation members extending therethrough while preventing buckling (e.g., movement toward the longitudinal axis of the outer shell) of the articulation members. Also, movement of the first and second articulation members up and down with respect to the longitudinal axis of the device is prevented.

Figure 7:
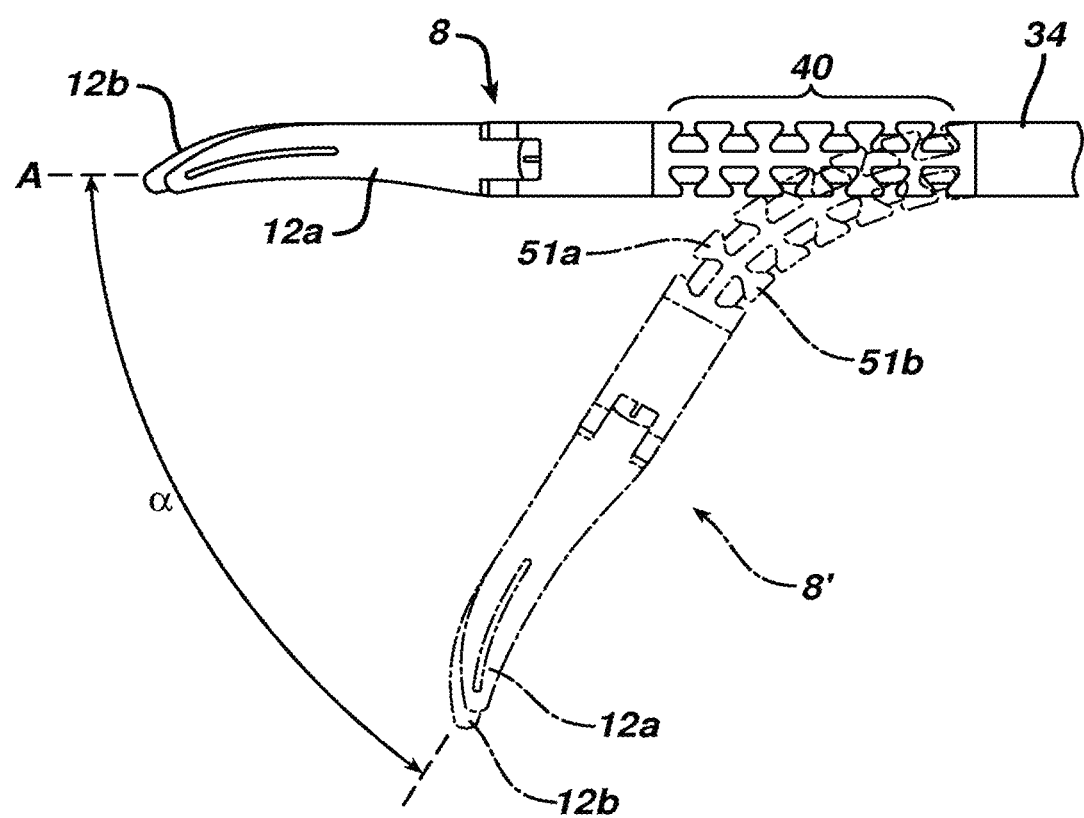
FIG. 7 is a top view of a distal portion of the flexible neck portion of the device of FIG. 1, showing the end effector both in an unarticulated position and in an articulated position.

FIG. 7 illustrates the flexible neck 40 and the end effector 8 coupled to a distal end of the flexible neck 40. First and second articulation members extend through the flexible neck 40 and are coupled to opposed sides of the end effector 8 such that axial translation of the articulation members within the flexible neck 40 is effective to cause the flexible neck 40 to bend such that the end effector 8 can be oriented to extend transverse, e.g., at an angle greater than 0, to a longitudinal axis of the elongate shaft 34.

FIG. 7 shows the end effector 8 in an unarticulated position, e.g., at a zero angle relative to the longitudinal axis of the elongate shaft 34. FIG. 7 also illustrates the end effector 8' in an articulated position, e.g., at an articulation angle α relative to the longitudinal axis A. The end effector 8 can of course move in an opposite direction as well. In some embodiments, the end effector 8 can articulate up to about 50 degrees to 60 degrees in each direction. However, the flexible neck can be configured to bend to any other angle.

The first series of flexible ribs 51a and the second series of flexible ribs 51b can deform during articulation of the flexible neck 40. For example, when the flexible neck 40 is articulated to the left, as shown in FIG. 7, the second series of flexible ribs 51b move toward one another while the first series of flexible ribs 51a move apart. Thus, when the flexible neck 40 is articulated to the left, a width of at least some of the second elongate slots 41b can decrease so that distances between at least some of the ribs of the second series of flexible ribs 51b become smaller. The distances between some of the ribs 51b that are near or at a bending point can decrease to a greater degree as compared to distances between other of the ribs 51b disposed farther away from the bending point. At the same time, a width of at least some of the first elongate slots 41a can increase so that distances between at least some of the ribs of the first series of flexible ribs 51a become greater. The distances between some of the ribs 51a that are near or at a bending point can increase to a greater degree as compared to distances between other of the ribs 51a disposed farther away from the pending point. The first series of flexible ribs 51a and the second series of flexible ribs 51b can be configured so as to substantially maintain their shape when they are bent, however, they can deform to some degree while still maintaining sufficient rigidity.

The end effector 702 of the surgical device can be articulated in a number of different ways. In one embodiment, first and second articulation members extending through the elongate shaft 34 and the flexible neck 40, and coupled to both sides of the end effector 8, can be operated as follows. To bend the end effector 8 to the left, as shown in FIG. 7, an articulation member coupled to the left side of the end effector 8 can be pulled proximally and another articulation member coupled to the opposite, right side of the end effector 8 can be pushed or allowed to move distally. In a similar manner, to bend the end effector 8 to the right, an articulation member coupled to the right side of the end effector 8 can be pulled proximally and another articulation band coupled to the opposite, left side of the end effector 8 can be pushed distally. Exemplary embodiments of methods and devices for actuating the surgical device are further described in U.S. application Ser. No. 14/658,944 (now U.S. Pat. No. 10,159,506) entitled "Methods and Devices for Actuating Surgical Instruments" filed on Mar. 16, 2015, which is hereby incorporated by reference in its entirety.

Surgical devices including a flexible neck assembly described herein can be manufactured in a variety of ways. In one exemplary embodiment, a method of manufacturing of the surgical device with a flexible neck assembly can include injection molding the outer shell 42 to form a substantially cylindrical monolithic component having a configuration as previously described herein. For example, an appropriately sized and configured injection mold can be used to create the outer shell via a single injection molding process. The method also includes injection molding each flexible divider 46a, 46b using a single mold and a single process to make each divider. The outer shell and dividers can be manufactured from a variety of material(s). For example, the outer shell can be made from a polyetherimide (PEI) material, such as ULTEM™ resin. Other non-limiting examples of material(s) that can be used include polycarbonate, nylon, high density polyethylene, polyester, polytetrafluoroethylene, polypropylene, and polyvinylchloride. The materials may allow a maximum stress in the range from about 15 kilo-pounds per square inch (ksi) to about 20 ksi to be achieved when bending the components. Such materials typically have higher-yield stresses and can allow manufacturing of a flexible section having a reduced length. For example, ULTEM™ has yield strength of 15 ksi and it has a higher modulus than some other materials. Thus, ULTEM™ can provide additional rigidity to the outer shell. Materials having lower-yield stresses can require a longer flexible section to be manufactured, to reduce stress. One skilled in the art will appreciate that the outer shell and dividers can be formed from any suitable material(s), and that the shell and the dividers can be formed from the same materials or from different materials.

Once the various components are formed, the first and seconds dividers 46a, 46b can be advanced into the inner lumen 44 of the outer shell 42 so that the dividers can be freely slidable relative to the shell. As discussed above, the dividers 46a, 46b separate the inner lumen 44 into elongate channels or pathways extending longitudinally through the lumen 44 so as to allow elongate actuating elements or shafts to be received therein. For example, with reference to FIGS. 4C and 6A, the dividers 46a, 46b can separate the inner lumen 44 into a first inner channel 70 formed between the dividers, a second inner channel 72 formed between the dividers 46a, 46b, a first outer channel 90 defined between brackets 78 and the inner surface of the first ribs 51a, a second outer channel 92 defined between brackets 80 and the inner surface of the second ribs 51b, and a bracket channel 96 defined through brackets 78.

With reference to FIG. 4D, after the divider 46 is advanced into the inner lumen 44 of the outer shell 42, a first articulation band 290 can be advanced through the elongate shaft 34 and through the first outer channel 90. Similarly, a second articulation band 292 can be advanced through the elongate shaft 34 and through the second outer channel 92. FIG. 4D illustrates that the first and second articulation bands 290, 292 are seated in cut-outs in brackets formed along the external surfaces of the dividers. The first and second articulation bands 290, 292 can be freely longitudinally slidable within the first and second outer channels 90, 92.

With continued reference to FIG. 4D, a cutting element 270 (e.g., knife) can be advanced through the elongate shaft 34 and through the first inner channel 70, and an actuation band 272 for opening and closing the first and second jaws can be advanced through the second inner channel 72. A conducting member or electrode 296 can be advanced through the elongate shaft 34 and through the bracket channel 96 formed through the brackets 78.

The flexible neck 40 can be assembled to the elongate shaft by coupling a proximal end 40p of the flexible neck 40 to a distal end of the elongate shaft 34, and by coupling a distal end 40d of the flexible neck 40 to a proximal end of the end effector 8. Various mating techniques known in the art can be used. The actuating elements, e.g., the first and second articulation bands, the cutting element, the actuation band, and the electrode, can extend through the elongate shaft 34 and can be coupled to suitable components within the handle or elsewhere that are configured to control operation of the actuating elements. Exemplary embodiments of methods and devices for actuating the surgical device are further described in U.S. application Ser. No. 14/658,944 (now U.S. Pat. No. 10,159,506) entitled "Methods and Device for Actuating Surgical Instruments" filed on Mar. 16, 2015, which is hereby incorporated by reference in its entirety.

Figure 8:
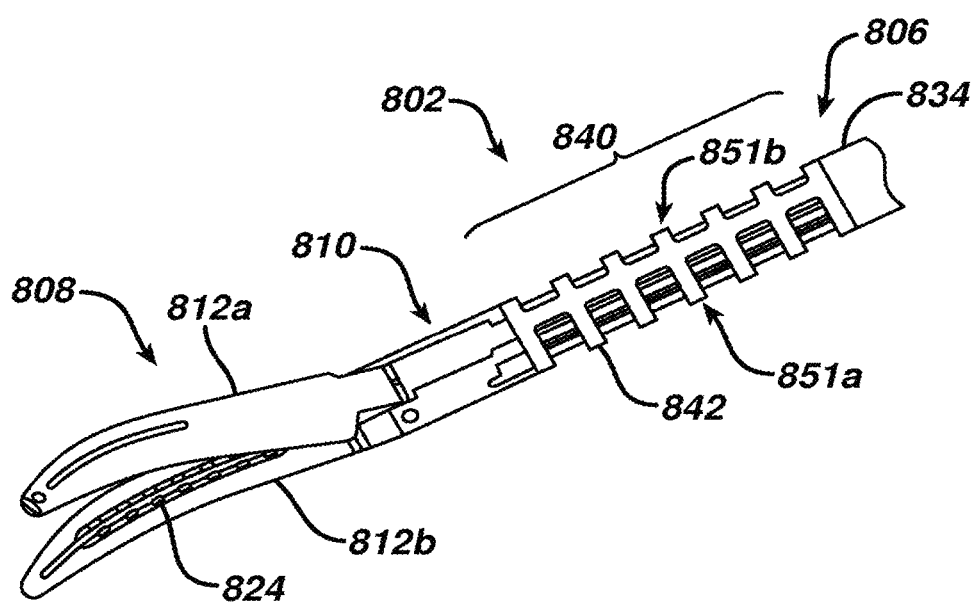
FIG. 8 is a perspective view of another embodiment of a distal portion of a surgical device.

FIG. 8 illustrates an alternative embodiment of a surgical device 802 including a flexible portion having an outer shell with ribs having a substantially constant width along a length thereof. The surgical device 802 is similar to surgical device 2 (FIGS. 1-3). As shown in FIG. 8, the surgical device 802 has a shaft assembly 806 and an end effector 808 that is coupled to a distal end of the shaft assembly 808. The end effector 808 can be coupled to the shaft assembly 806 at a pivot joint 810. The end effector 808 includes a first upper jaw 812a and a second lower jaw 812b. One or both of the jaws 812a, 812b can include electrodes 824.

The shaft assembly 806 of the surgical device 802 includes an elongate shaft 834 and a flexible neck portion 840 extending between the elongate shaft 834 and a proximal end of the end effector 808. Similar to outer shell 42 (e.g., FIGS. 2 and 3), the outer shell 842 can include two rows of slots formed in opposite sides thereof that define first and second opposed longitudinal spines and first and second rows of arcuate ribs extending between the spines along a circumference of the outer shell 842. However, as shown in FIG. 8, each rib of a first series of arcuate ribs 851a disposed along one side of the outer shell 842 and a second series of arcuate ribs 851b disposed along another side of the outer shell 842 can have a width that is substantially constant along the entire length of the rib. Elongate slots defined between the ribs 851, 851b can similarly have a substantially constant width along a length thereof. Furthermore, it should be appreciated that an outer shell of a flexible portion in accordance with the described techniques can be in the form of ribs that can have any other suitable shape. Furthermore, the width of the ribs can vary in different ways along a length thereof. Regardless of the shape of the ribs, the flexible portion can be configured to bend to thereby cause the end effector 808 to articulate.

The flexible portion 840 of the embodiment of FIG. 8 can include any other components and features, such as at least one divider, for slidably and non-fixedly retaining the divider(s) within the outer shell 842. The flexible portion 840 can have articulation bands and other elongate members extending therethrough from the elongate shaft 834 and configured to articulate the end effector 808 or cause other movement of the end effector.

In some embodiments, an outer shell of a flexible portion of a surgical device can include different ribs at opposite sides thereof. In such embodiments, the flexible portion can be configured to bend in one direction but not in the other. As another variation, the flexible portion can be configured to bend at a greater angle to one direction as compared to a bent angle to the opposite direction.

Figure 9:
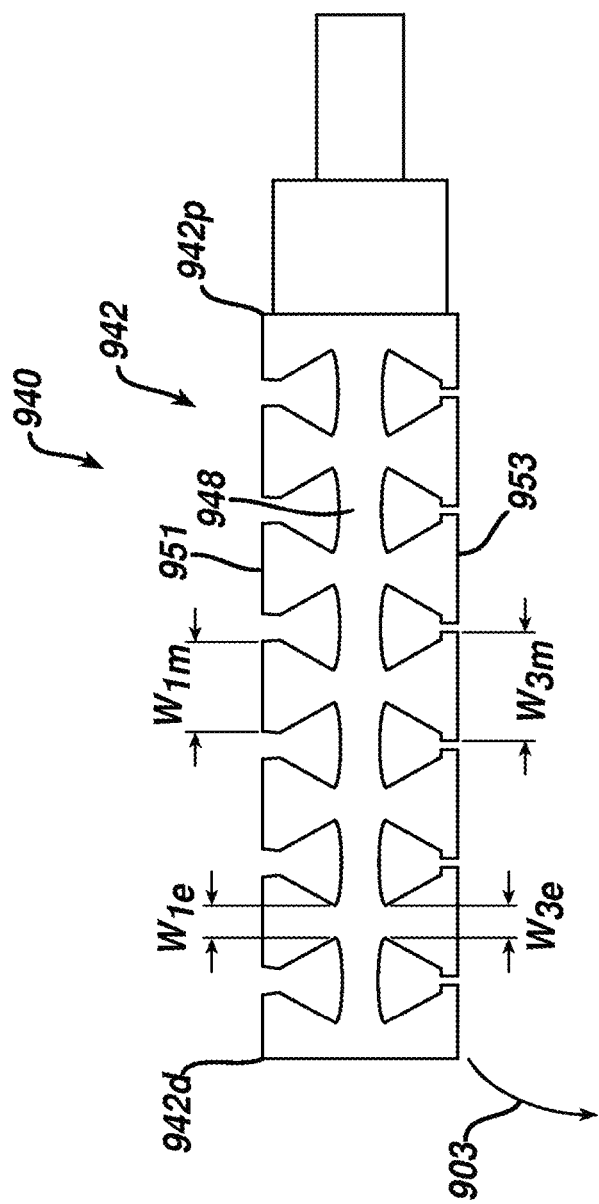
FIG. 9 is a top view of another embodiment of an outer shell of a flexible portion of a surgical device.

FIG. 9 illustrates another embodiment of an outer shell 942 of a flexible portion 940 of a surgical device. The surgical device can be any suitable device, for example, it can be similar to surgical device 2 (FIGS. 1-3). As shown in FIG. 9, the outer shell 942 having proximal and distal ends 942p, 942d includes a first series of arcuate ribs 951 disposed along one side of the outer shell 942 and a second series of arcuate ribs 953 disposed along another side of the outer shell 942. The first and second series of arcuate ribs 951, 953 can be spaced apart longitudinally along opposite sides of the outer shell 942 and each rib extends between upper and lower spines (the upper spine 948 is shown) at least partially around the circumference of the outer shell 942.

As shown in FIG. 9, the arcuate ribs 951, 953 are configured such that their mid-portion has a width that is greater than a width at an end portion adjacent to each of the upper and lower spines. As shown, the arcuate ribs 951, 953 have approximately the same widths W1e, W3e at their end portions adjacent the upper spine 948. However, they have different widths at the respective mid-portions thereof. Thus, as shown, a mid-portion W3m of each of the second ribs 953 is greater than a mid-portion W1m of each of the first ribs 951. Thus, the configuration of the arcuate ribs 951, 953 is such that the flexible portion 940 can be configured to bend to the left (shown by an arrow 903) but it can be entirely or partially prevented from bending in the opposite (right) direction shown by an arrow 905.

One skilled in the art will appreciate that the ribs can be configured such that the flexible portion can instead bend to the right while being entirely or partially prevented from bending to the left. It should be appreciated that the flexible portion can be configured such that a width of the arcuate ribs can vary along their length in any suitable manner and to any suitable degree so as to allow the flexible portion to have any preferred bending direction and/or so as to allow the flexible portion to bend in any desired manner.

A person skilled in the art will appreciate that the techniques described herein have application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the embodiments described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of manufacturing a medical device, the method comprising:

injection molding a substantially cylindrical monolithic outer shell such that the substantially cylindrical monolithic outer shell has an inner lumen extending longitudinally therethrough and a plurality of ribs spaced longitudinally along the substantially cylindrical monolithic outer shell and extending partially circumferentially around the substantially cylindrical monolithic outer shell with elongate slots separating each rib;

injection molding at least one flexible divider;

advancing the at least one flexible divider into the inner lumen of the substantially cylindrical monolithic outer shell such that the at least one flexible divider separates the inner lumen into first and second elongate channels, the at least one flexible divider being freely slidable relative to the substantially cylindrical monolithic outer shell;

mating a proximal end of the substantially cylindrical monolithic outer shell to a distal end of an elongate shaft, and mating a distal end of the substantially cylindrical monolithic outer shell to a proximal end of an end effector;

advancing a first articulation band through the elongate shaft and through the first elongate channel, and advancing a second articulation band through the elongate shaft and through the second elongate channel, the first and second articulation bands being freely longitudinally slidable within the first and second elongate channels;

mating the first and second articulation bands to opposed sides of the end effector; and advancing a conducting member through a plurality of longitudinally spaced brackets formed on an external surface of the at least one flexible divider.

2. The method of claim 1, wherein injection molding at least one flexible divider comprises injection molding first and second dividers.

3. The method of claim 2, further comprising advancing a knife through a first pathway formed between the first and second dividers, and advancing an actuation band through a second pathway formed between the first and second dividers.

4. The method of claim 2, wherein the first and second dividers have spacers formed thereon that maintain the first and second dividers at a predetermined distance apart.

5. The method of claim 1, wherein the substantially cylindrical monolithic outer shell has an upper spine and a lower spine, each extending along at least a portion of a length of the substantially cylindrical monolithic outer shell, and wherein the plurality of spaced ribs comprises a first plurality of spaced ribs extending between the upper and lower spines along a first side of the substantially cylindrical monolithic outer shell, and a second plurality of spaced ribs extending between the upper and lower spines along a second side of the substantially cylindrical monolithic outer shell.

6. The method of claim 1, wherein the first and second articulation bands are each advanced into a channel at least partially formed by an inner sidewall of the substantially cylindrical monolithic outer shell.

* * * * *